(12) United States Patent
Kulli

(10) Patent No.: US 7,534,227 B2
(45) Date of Patent: May 19, 2009

(54) NEEDLE TIP PROTECTOR

(75) Inventor: John C. Kulli, Hamlin, NY (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

(21) Appl. No.: 11/562,204

(22) Filed: Nov. 21, 2006

(65) Prior Publication Data

US 2007/0149928 A1    Jun. 28, 2007

Related U.S. Application Data

(62) Division of application No. 10/906,171, filed on Feb. 5, 2005, now Pat. No. 7,347,838.

(60) Provisional application No. 60/544,843, filed on Feb. 13, 2004.

(51) Int. Cl.
*A61M 5/178* (2006.01)

(52) U.S. Cl. ................................................ 604/164.08

(58) Field of Classification Search .................. 604/110, 604/164.01, 164.08, 192, 263, 194
See application file for complete search history.

(56) References Cited

U.S. PATENT DOCUMENTS

| | | | |
|---|---|---|---|
| 4,929,241 A | 5/1990 | Kulli |
| 4,952,207 A | 8/1990 | Lemieux |
| 4,964,854 A | 10/1990 | Luther |
| 5,013,305 A | 5/1991 | Opie et al. |
| 5,279,591 A | 1/1994 | Simon |
| 5,342,310 A | 8/1994 | Ueyama et al. |
| 5,419,766 A | 5/1995 | Chang et al. |
| 5,458,658 A | 10/1995 | Sircom |
| 5,584,809 A | 12/1996 | Gaba |
| 5,599,310 A | 2/1997 | Bogert |
| 5,683,365 A | 11/1997 | Brown et al. |
| 5,718,688 A | 2/1998 | Wozencroft |
| 5,882,337 A | 3/1999 | Bogert et al. |
| 5,935,109 A | 8/1999 | Donnan |
| 6,012,213 A | 1/2000 | Chang et al. |
| 6,203,527 B1 | 3/2001 | Zadini et al. |
| 6,224,569 B1 | 5/2001 | Brimhall |

(Continued)

FOREIGN PATENT DOCUMENTS

EP    0352928 A1    1/1990

(Continued)

OTHER PUBLICATIONS

Tawian Search Report (in its native language and an English translation) for ROC (Taiwan) Patent Application No. 094104277 (2 pages).

(Continued)

*Primary Examiner*—Kevin C Sirmons
*Assistant Examiner*—Catherine N Witczak
(74) *Attorney, Agent, or Firm*—Wood, Herron & Evans, LLP

(57) ABSTRACT

A needle tip protector (10, 10') including a pair of apertured members (28, 30 or 28', 30') with spring arms (22, 24) urging the apertured members (28, 30 or 28', 30') out of alignment to create a barrier to a needle tip (16). A needle gripping U-shaped clip (81) may also provide a needle tip protector (80).

19 Claims, 7 Drawing Sheets

U.S. PATENT DOCUMENTS

| | | | |
|---|---|---|---|
| 6,280,419 | B1 | 8/2001 | Vojtasek |
| 6,595,954 | B1 | 7/2003 | Luther et al. |
| 6,595,955 | B2 | 7/2003 | Ferguson et al. |
| 6,616,630 | B1 | 9/2003 | Woehr et al. |
| 6,652,486 | B2 * | 11/2003 | Bialecki et al. ............. 604/110 |
| 6,652,490 | B2 | 11/2003 | Howell |
| 6,709,419 | B2 | 3/2004 | Woehr |
| 6,749,588 | B1 | 6/2004 | Howell et al. |
| 6,981,965 | B2 | 1/2006 | Luther et al. |
| 2002/0177818 | A1 | 11/2002 | Vaillancourt |
| 2003/0195475 | A1 | 10/2003 | Ferguson et al. |
| 2004/0204681 | A1 * | 10/2004 | Thoresen et al. ....... 604/164.08 |
| 2004/0236288 | A1 | 11/2004 | Howell et al. |
| 2005/0075609 | A1 * | 4/2005 | Latona .................. 604/164.08 |

FOREIGN PATENT DOCUMENTS

| | | | |
|---|---|---|---|
| EP | 12509743 | A1 | 4/2002 |

OTHER PUBLICATIONS

European Search Report and Written Opinion for EP Patent Application No. 07002156.3, mailed Jun. 18, 2007 (8 pages).

Search Report and Written Opinion from related Singapore Patent Application No. 200605190-8 mailed May 9, 2008 (9 pages).

* cited by examiner

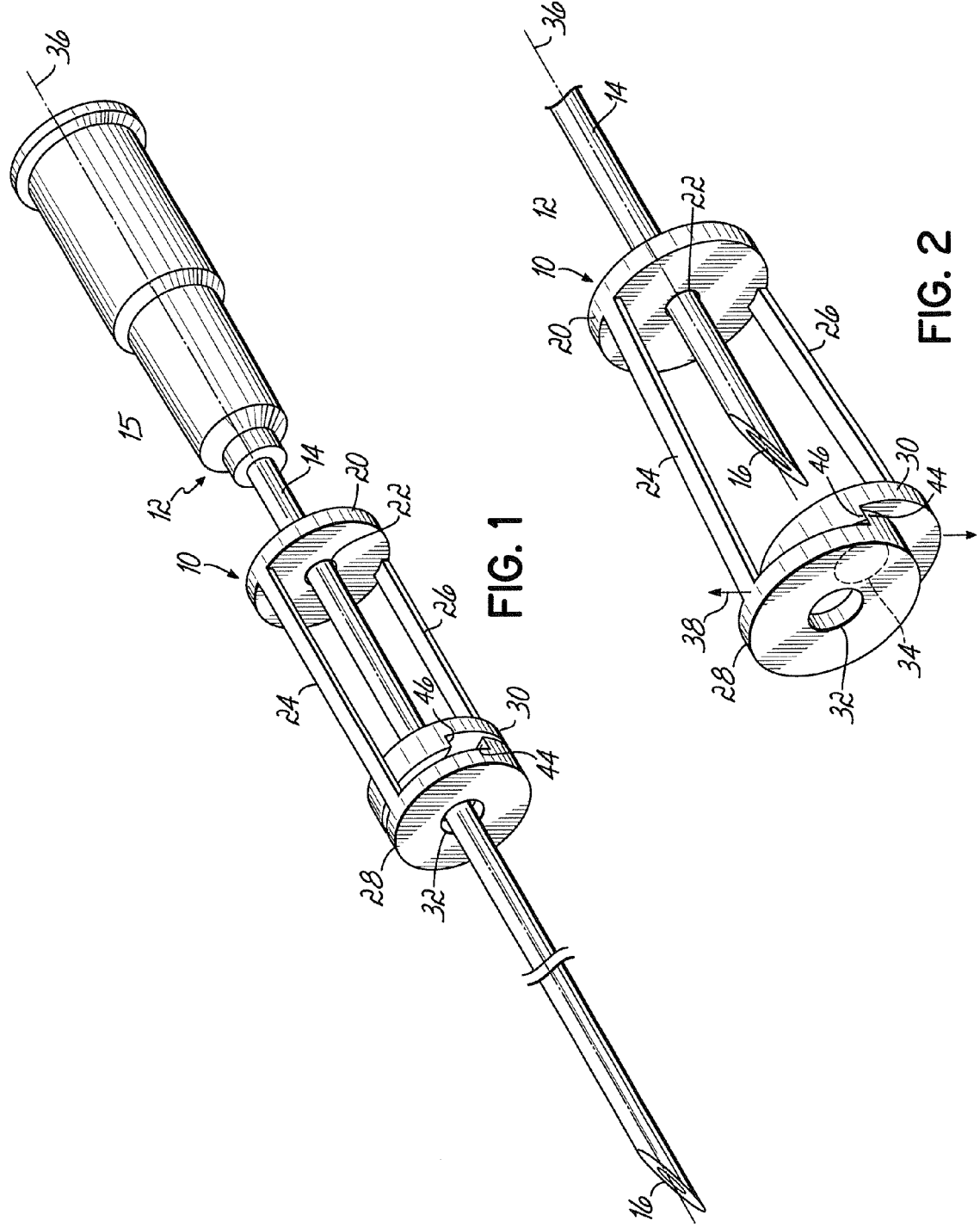

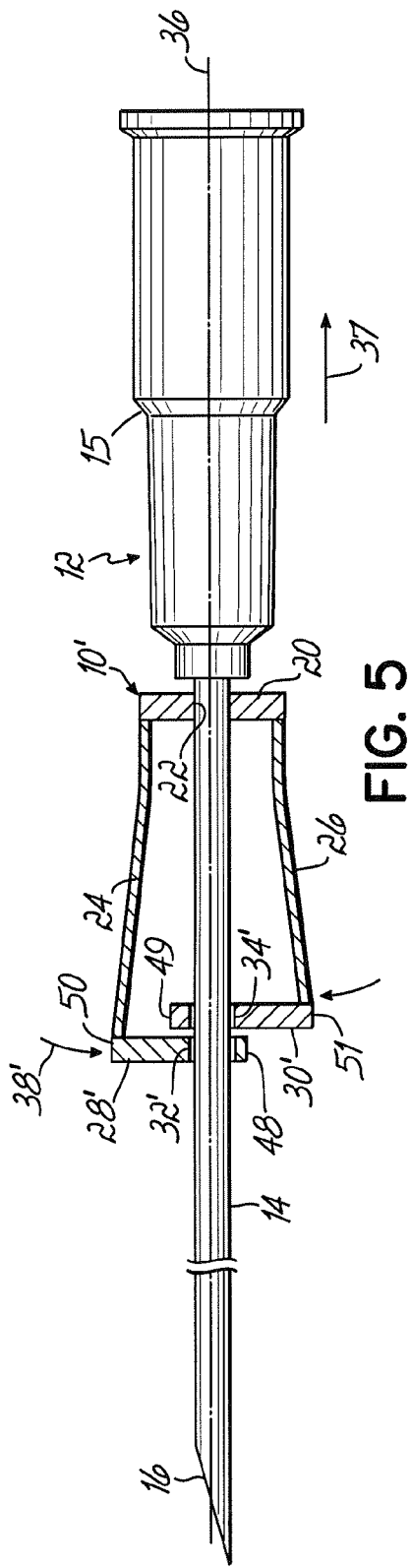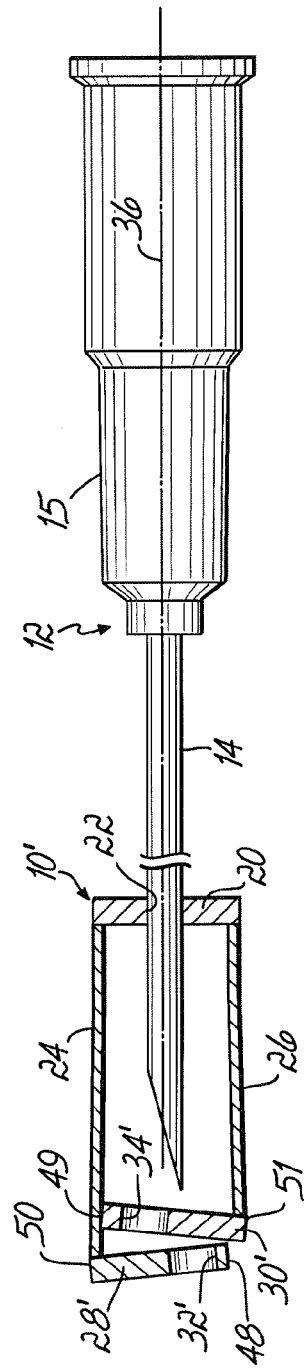
FIG. 5
FIG. 6

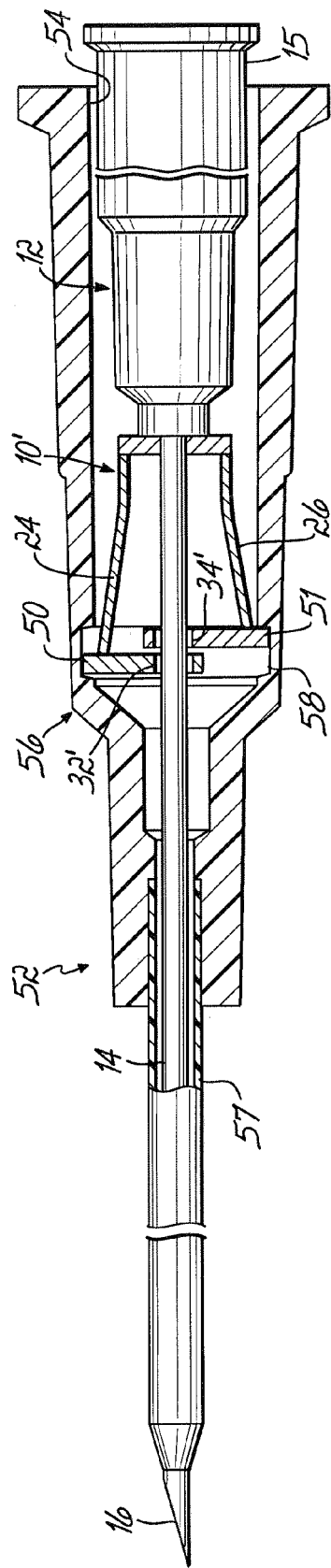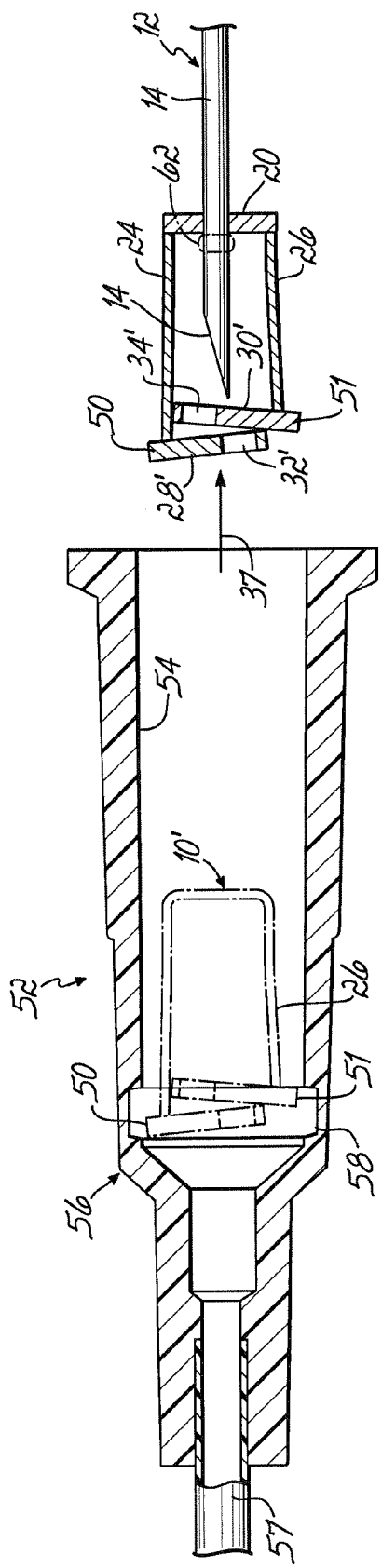
FIG. 7
FIG. 8

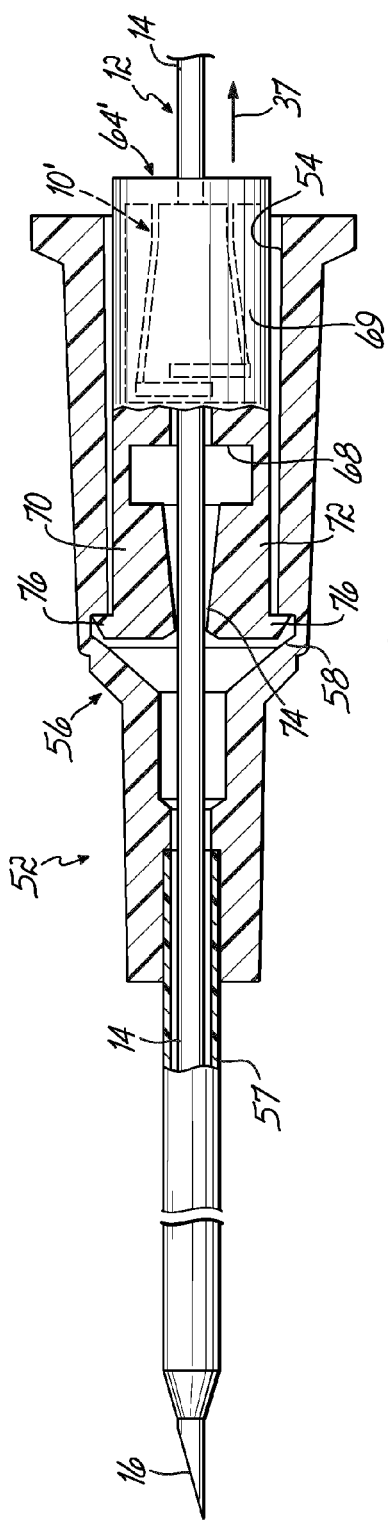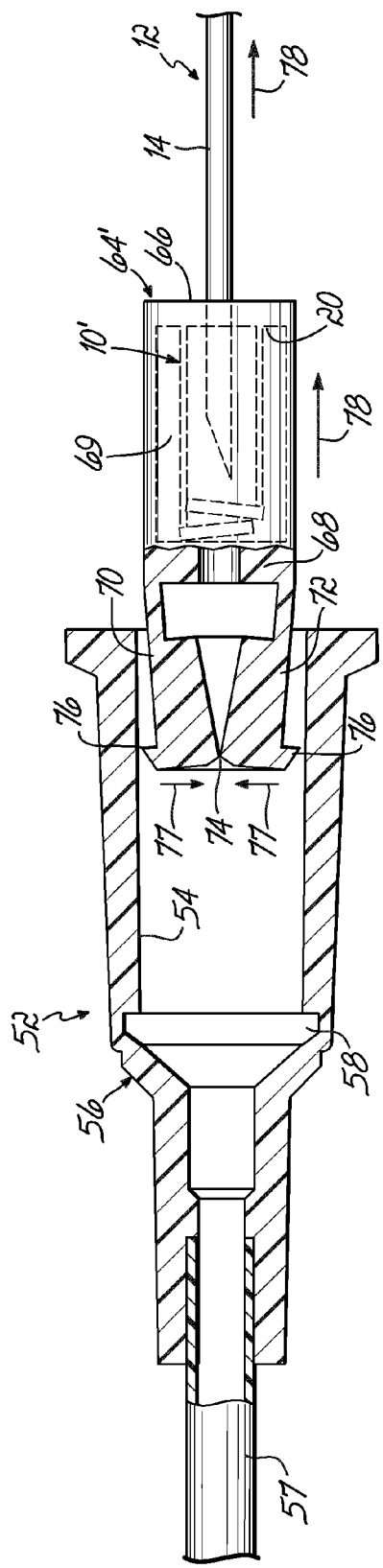

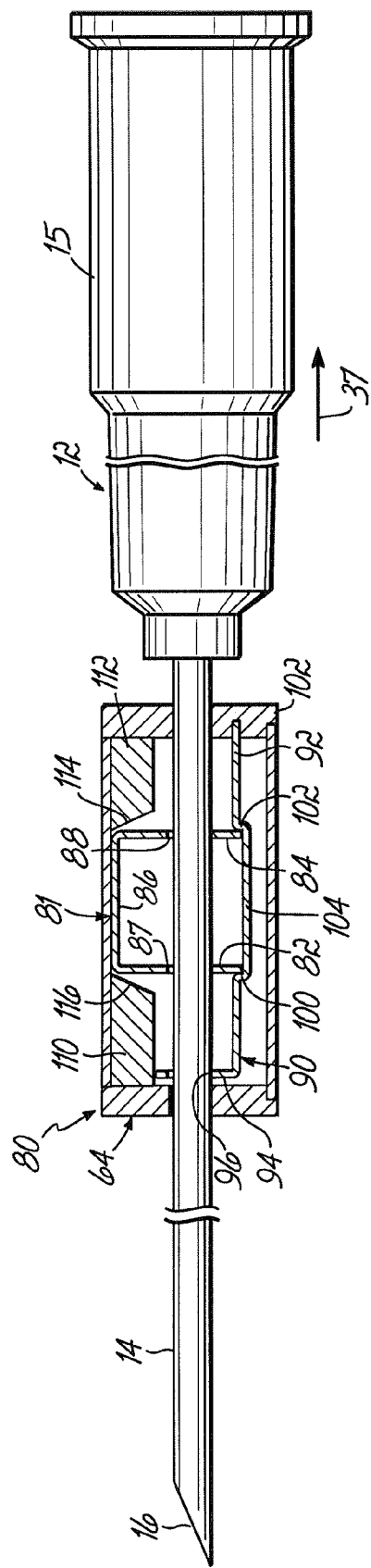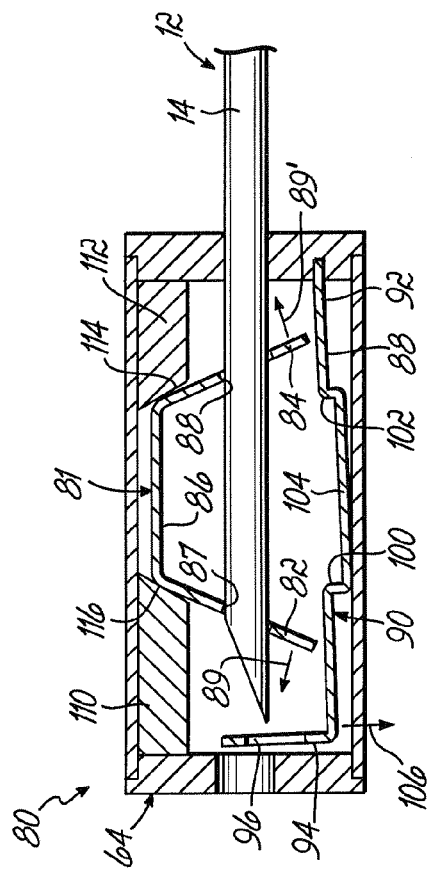
FIG. 12
FIG. 13

NEEDLE TIP PROTECTOR

CROSS-REFERENCE TO RELATED APPLICATION

This application is a divisional of U.S. patent application Ser. No. 10/906,171, filed Feb. 5, 2005, which claims the benefit of U.S. Provisional Application No. 60/544,843, filed Feb. 13, 2004, the disclosure of which is incorporated by reference herein in its entirety.

FIELD OF THE INVENTION

The present invention relates to medical needles and, more particularly, to devices for protecting against the sharp tip of the needle.

DESCRIPTION OF PRIOR ART

Needles (to include all sharp-tipped cannulae) are used throughout the medical profession for a variety of medical procedures. For example, hypodermic needles are used with syringes to administer fluids and/or medications to patients and to withdraw fluids from patients. Similarly, sharp-tipped cannula are used to insert catheters into patients for various medical purposes. An intravenous catheter may typically include a sharp-tipped needle cannula with its shaft extending through the catheter so that the sharp tip extends slightly beyond the distal end of the catheter. The other end of the needle is connected to a hub or other structure which is held by the healthcare worker during insertion. The needle hub is typically fitted into the catheter hub. The needle and catheter are inserted together into the patient until the catheter end is properly placed in the patient's blood vessel. The needle hub is pulled from the catheter hub to withdraw the needle, leaving the catheter in place in the patient for administration or withdrawal of fluids or other medically required procedures or purposes. But as with hypodermic needles, after use, the exposed sharp tip of the needle cannula presents a source of accidental needle-stick, which may cause injury or disease, such as by transmission of dangerous blood-borne pathogens.

A variety of different devices intended to enclose or otherwise shield the sharp needle tip have been developed in recognition of the need to reduce or eliminate accidental needle-sticks. While many of these devices provide advantages, further enhancements are desired.

SUMMARY OF THE INVENTION

The present invention provides needle tip protectors which provide further enhancements over prior approaches. To this end, and in accordance with one aspect of the present invention, a support is telescopingly received over the needle shaft and includes a pair of spring arms each supporting at its end an apertured member adapted to extend into the axis of the needle, with the members being normally urged by the spring arms into a position where the apertures thereof are out of alignment with the needle axis, but which are held in alignment when a needle shaft is extending through the apertures. Thus, when the needle shaft is retracted from the loaded position in which it is extending through the apertures to an unloaded position, the spring arms urge the apertured members out of alignment so as to create a barrier against moving the needle back into the loaded position.

In accordance with a different aspect of the present invention, needle gripping structure is provided to secure the needle in the unloaded position. In one embodiment, the needle shaft may include an irregularity defining an oversized portion near the sharp tip with the support having an aperture sized to prevent the irregularity from passing through the support when the needle moves from the loaded to the unloaded position. As a consequence, when the needle is pulled to the unloaded position, the tip end becomes trapped between the now-misaligned aperture members and the support. In still other embodiments, the needle gripping structure may be active, such as provided by an extension flange or projection which grips into a slot in the needle such as shown in European Patent No. 0 352 928 B2, a locking clip such as shown in U.S. Pat. No. 5,328,482, or other mechanisms such as shown in aforesaid U.S. Pat. No. 5,328,482, or U.S. Pat. Nos. 5,458,658; 611,781; or 5,662,610. The disclosures of all of the foregoing U.S. and European patents are incorporated herein by reference in their entireties.

In a still further embodiment of the invention, the needle gripping structure may provide a needle tip protector in the form of a generally U-shaped clip having an aperture in each leg thereof for the needle shaft to pass easily therethrough when the clip is in a first state and to grip the needle shaft in a second state of the clip with one or both of the legs being angularly offset from the position the leg(s) held in the first state of the clip. The clip may be resilient so that it normally tends towards the second state. A trigger mechanism may be provided which cooperates with the needle shaft so as to hold the clip in the first state when the needle is in the loaded state and to release the clip when the needle releases from the trigger so as to allow the clip to go into the second state thereby to grip the needle. Cam structure may also be provided to assist in urging the clip leg(s) into the angular offset position to tighten the grip on the needle shaft as the needle shaft is moved while in the unloaded position. Advantageously, a surface of the cam is at an angle relative to a plane perpendicular to the needle shaft to facilitate such tightening of the grip.

In accordance with a yet further, different aspect of the present invention, the support may be defined by an aspect of a housing which telescopingly receives the needle. Further the needle gripping structure may be contained, at least in part, within the housing.

When the needle tip protector is to be used with a catheter, it is advantageous to have the needle tip protector remain affixed with the catheter hub until or with the needle being moved into the unloaded position. To this end, and in accordance with a still additional, different aspect of the present invention, features of the needle tip protector or its housing are urged against the interior surface of the catheter hub when the needle shaft is passing therethrough such as in the loaded state of the needle, and which are biased to move away from the catheter hub interior wall when the needle shaft is no longer passing therethrough so as to release from the catheter hub. In one embodiment, the apertured members could be held so as to have aspects thereof extend outwardly into the catheter hub interior wall, such as an annular recess therein, in the loaded position of the needle such that they are urged together when the needle departs the loaded state, so as to release from the catheter hub. In another embodiment, the apertured members may be held with a housing having resilient fingers extending therefrom and which have detents to engage the catheter hub interior wall when flexed apart by the needle shaft passing therethrough.

By virtue of the foregoing there are thus provided needle tip protectors which provide further enhancements over prior approaches. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

FIG. 1 is a perspective view of a first embodiment of a needle tip protector of the present invention in the needle loaded state;

FIG. 2 is a view similar to FIG. 1 showing the needle tip protector of FIG. 1 in the needle unloaded state and defining a barrier to the needle tip;

FIG. 5 is an axial cross-sectional view of a second embodiment of a needle tip protector of the present invention in the needle loaded state;

FIG. 6 is a view similar to FIG. 5 showing the needle tip protector of FIG. 5 in the needle unloaded state and defining a barrier to the needle tip;

FIG. 7 is a partial, cross-sectional side view of the needle tip protector of FIG. 6 associated with a catheter and affixed to the hub thereof in accordance with the principles of the present invention;

FIG. 8 is a view similar to FIG. 7 showing release of the needle tip protector from the catheter hub;

FIG. 10 is a partial, cross-sectional side view of the needle tip protector and housing of FIG. 9 with catheter hub engagement fingers shown held to a catheter hub in the needle loaded position;

FIG. 11 is a view similar to FIG. 10 showing the hub engagement fingers released from the catheter hub in the needle unloaded position;

FIG. 12 is an axial cross-sectional view of a third embodiment of a needle tip protector in accordance with the principles of the present invention in the needle loaded state; and FIG. 13 is a view similar to FIG. 12 in the needle unloaded state.

DETAILED DESCRIPTION OF THE DRAWINGS

Figure 3:
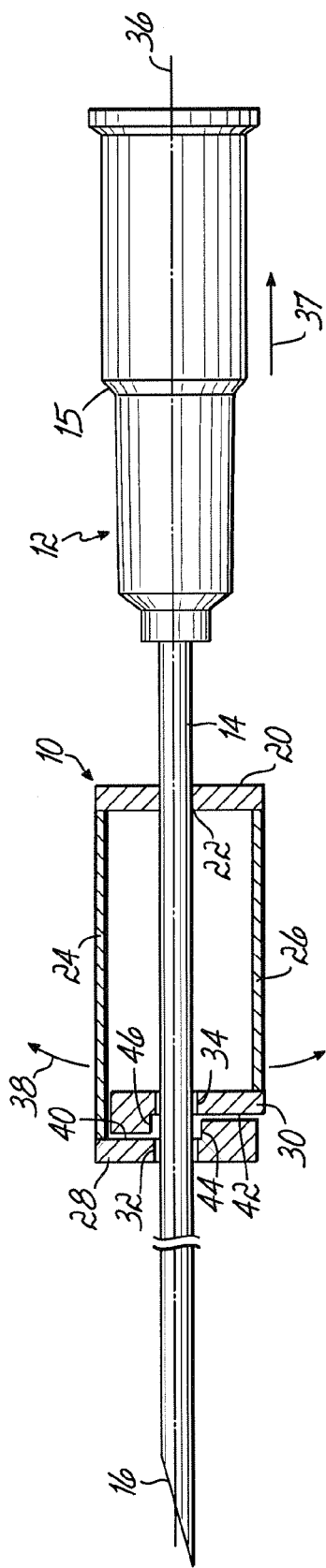
FIG. 3 is an axial cross-sectional view of the needle tip protector of FIG. 1.

With respect to FIGS. 1-4 there is shown a first embodiment 10 of a needle tip protector intended to cooperate with a needle 12 having a shaft 14 extending from a needle hub 15, and a sharp tip end 16. Needle tip protector 10 includes a support member 20 such as a wall or disk (or multiple, overlapping elements, not shown) having or defining an aperture 22 telescopingly receiving shaft 14 of needle 12. A pair of spring arms 24, 26 which may be wires, thin strips, or wide bands, extend from support 20 in a direction toward sharp tip 16. A pair of apertured members 28, 30 are connected to respective ones of the spring arms 24 and 26. Apertured members may be walls or other such structure, and may advantageously be in the form of circular discs as shown in FIG. 1. Members 28 and 30 each has a respective aperture 32, 34, such as a circular or other shaped hole, therein sized to receive therethrough shaft 14 of needle 12.

Members 28, 30 may be pushed into alignment, such as by being urged radially inwardly relative to each other by an external force, so that holes 32 and 34 thereof are in alignment with a common axis such as the longitudinal axis 36 of needle 12. As so-aligned, needle shaft 14 is telescopingly received through support aperture 22 and holes 32, 34 of apertured members 28, 30 to define a loaded position of needle 12 as shown in FIG. 1. Spring arms 24, 26 tend to urge disks 28 and 30 apart so that apertures 32, 34 try to move out of alignment from common axis 36. To this end, when needle 14 is retracted (as indicated by arrow 37 in FIG. 3) from the loaded position of FIGS. 1 and 3 to an unloaded position, such as shown in FIGS. 2 and 4, shaft 14 comes out of aperture 32, and possibly aperture 34 depending upon the design and the spacing between apertured members 28 and 30, so as to allow one or both of the members 28, 30 to move radially outwardly (as exemplified by arrow 38 in FIGS. 2 and 3) and out of the alignment with axis 36 of needle 12. In the unloaded position, apertured members 28, 30 are out of alignment so as to provide a barrier against moving needle tip 16 back into the loaded position of needle 12.

Figure 4:
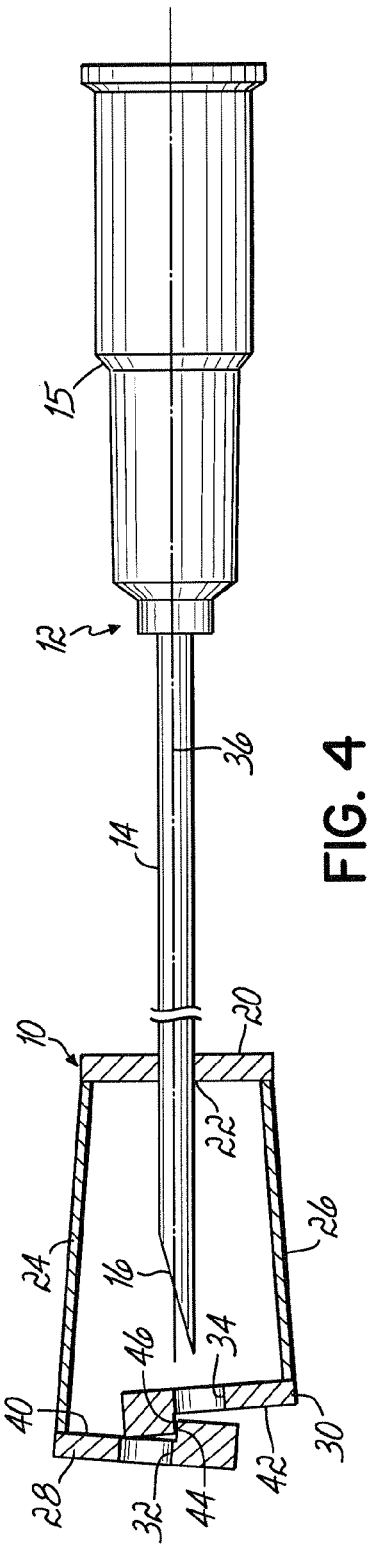
FIG. 4 is an axial cross-sectional view of the needle tip protector of FIG. 2.

In order to limit misalignment of apertured members 28 and 30 so, for example, they do not come too far apart and create a gap therebetween for re-emergence of needle tip 16, members 28 and 30 may advantageously extend in a direction transverse or perpendicular to the axis 36 of needle shaft 14 such that they define confronting faces 40, 42 each of which is provided with a respective ledge 44, 46 which are in opposed positions (FIGS. 3 and 4). As seen in FIG. 3, in the loaded position of needle 12, ledges 44 and 46 may be spaced apart such as to either side of needle shaft 14. However, with needle 12 moved to the unloaded position, shown by way of example in FIG. 4, one or both of members 28 and 30 are free to move radially out of alignment due to the action of spring arms 24, 26. However, the extent of outwardly radial movement is limited by the ledges 44, 46 which cooperate such as by impacting against one another.

While apertured members 28, 30 of tip protector 10 are shown as moving inwardly to align and outwardly to misalign, the opposite directions of movement could also be utilized. To this end, and with reference to FIGS. 5 and 6, it will be seen that an alternative embodiment 10' of needle tip protector has apertured members 28' and 30' with apertures 32' and 34' offset so as to be closer towards edges 48, 49 than edges 50, 51, the latter being near or where the spring arms 24, 26 attach. Members 28' and 30' may be disc-shaped such as ovoid or circular and are moved radially outwardly relative to each other so as to align the apertures 32', 34' for needle 12 to telescope therethrough in the loaded position as seen in FIG. 5. Spring arms 24, 26 urge the members 28', 30' together (as indicated by arrow 38' in FIG. 5) such that when needle 12 moves (as indicated by arrow 37 in FIG. 5) out of the loaded position to an unloaded position, as shown by way of example in FIG. 6, apertured members 28' and 30' move radially inwardly relative to each other so as to go out of alignment with needle axis 36 and to thus provide the desired barrier to reemergence of needle tip 16. In embodiment 10', no ledges are required due to presence of spring arm 24 against which member 30' may impact, for example, although ledges could be provided.

A further aspect of tip protector 10' facilitates its use with a catheter 52. In particular, and with reference to FIG. 7, it can be seen that in the loaded position of needle 12, one or more of edges 50, 51 of members 28', 30' are urged against the interior wall 54 of catheter hub 56, to grip thereat. Edges 50, 51 may additionally or alternatively be received into a recess 58 (which may be annular) of catheter hub wall 54. Edges 50, 51 may be the peripheral portions of members 28', 30' or may be projecting elements attached thereto or formed thereon. As a consequence, in the loaded position of needle 12 such as with needle 12 extending through catheter tube 57 such that needle tip 16 projects therefrom, tip protector 10' is within and held to catheter hub 56. Although not shown, it will be appreciated that needle hub 15 may form part of, be attached to, or communicate into, a flashback chamber. When needle 12 is moved (in the direction of arrow 37 in FIG. 8) into the unloaded state, as seen in FIG. 8, members 28', 30' move radially inwardly so as to not only provide a barrier to re-emergence to needle tip 16, but also to come away from catheter hub wall 54 thereby allowing tip protector 10' to easily come away from catheter hub 56.

Shaft 14 of needle 12 may be provided with an irregularity 62 (shown in dotted line in FIG. 8), such as a crimp, a bump or other projecting feature to define an oversized portion of shaft 14, near tip 16. Aperture 22 of support member 20 may be sized so as to prevent irregularity 62 from pressing therethrough such that in the unloaded position of needle 12 as seen in FIG. 8, the tip end 16 is captured between members 28' 30' (or members 28, 30 where protector 10 is used) and support member 20. If the irregularity 62 is present, it must be small enough to go through apertures 32' and 34' but not so small as to go through aperture 22 in support wall 20. Further, apertures 32' and 34' (or 32 and 34) may need to have their openings shaped to help cam the irregularity into the aperture on withdrawal of the needle from the loaded state.

Figure 9:
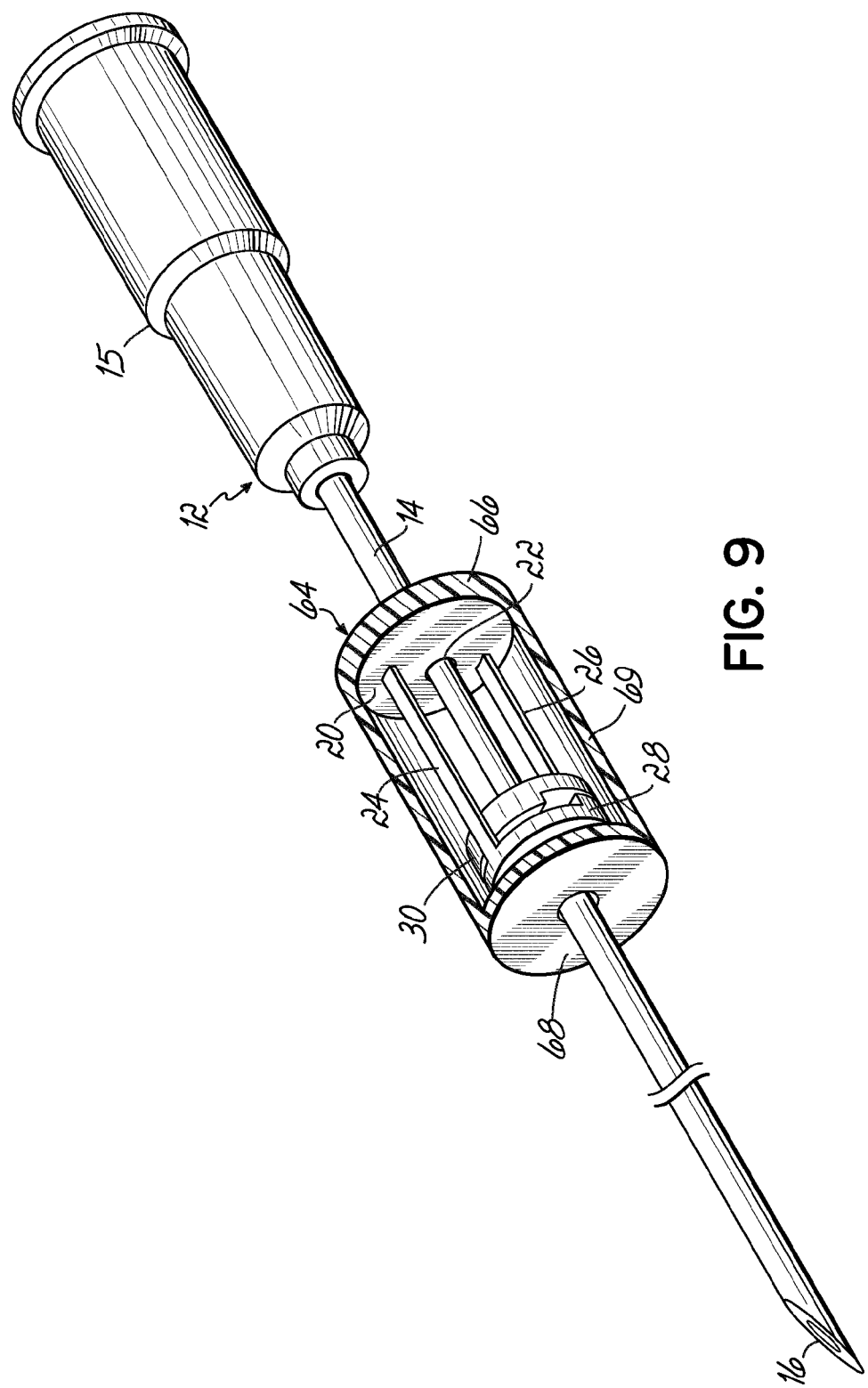
FIG. 9 is a perspective, particularly cut-away view of the needle tip protector of FIG. 1 with a housing.

Alternatively or additionally, a housing 64 may be provided, with proximal wall 66 thereof defining support member 20 as seen in FIG. 9. Alternatively, spring arms 22, 24 could extend from the distal wall 68 of housing 64, such that wall 68 defines support 20. Housing 64 may be a cylindrical or other shaped plastic or metal structure including a sidewall 69 extending distally of proximal wall 66 as seen in FIG. 9. Housing 64 is designed to be telescopingly received over needle shaft 14 with needle tip 16 extending therefrom. Housing 64 thus provides a cover to needle tip 16 within protector 10, and to protector 10 to reduce the likelihood that apertured members 28, 30 might be pushed back together and allow for re-emergence of needle tip 16. Depending on size, housing 64 may also be received in catheter hub 56. Tip protector 10 and 10' may be of metal and/or plastic. For example, members 28, 30 or 28', 30' and spring arms 24, 26 may be metal, and support member 20 may be metal or may be plastic, especially if housing 64 is formed of plastic.

Housing 64 may be modified to housing 64' as shown in FIG. 10 to include resilient fingers 70, 72 extending from distal wall 68 of housing 64 and being normally biased radially inwardly such as to be urged together. The area 74 defined between fingers 70, 72 is normally less than the diameter of needle shaft 14, such that with shaft 14 telescoped therethrough as seen in FIG. 10, fingers 70, 72 are held radially outwardly and against catheter hub interior wall 54 so as to hold housing 64 to catheter hub 56. Advantageously fingers 70, 72 each include detents 76 adapted to engage into recess 58 of catheter hub 56 so as to improve the hold. When needle 12 is moved (in the direction of arrow 37 in FIG. 10) into the unloaded position as shown in dashed line in FIG. 11, needle shaft 14 is no longer holding fingers 70 and 72 fully apart, so they move back towards each other (as indicated by arrows 77 in FIG. 11), releasing the hold on catheter hub 56, to thus allow for easy release from catheter hub 56 upon further pulling of needle 12 away from catheter hub 56 as indicated by arrows 78 in FIG. 11. The structure and operation of fingers 70, 72 may be as shown in U.S. Pat. No. 5,599,310 the disclosure of which is incorporated herein by reference in its entirety. Housing 64' may be sized to include tip protector 10 or 10' (only protector 10' is shown, in dashed line, in FIGS. 10 and 11 for reference purposes) and to fit either within or outside of catheter hub 56, the former when the apertured members 28, 30 or 28', 30' are also sized to fit within hub 56.

Needle tip 16 may be held within housing 64 or 64' due to an irregularity 62 (see FIG. 8). Housing 64 or 64' may additionally, or alternatively, include therein structure to actively grip shaft 14 of needle 12, especially once needle 12 has assumed the unloaded state. Some examples are an extension flange or projection which grips into a slot in the needle such as shown in European Patent No. 0 352 928 B2, a locking clip such as shown in U.S. Pat. No. 5,328,482, or other mechanisms such as shown in aforesaid U.S. Pat. No. 5,328,482, or U.S. Pat. Nos. 5,458,658; 611,781; or 5,662,610. Alternatively, and in accordance with a further aspect of the present invention, a third embodiment 80 of a needle tip protector is provided by an active needle gripping structure in the form of a U-shaped clip 81 as will now be described with reference to FIGS. 12 and 13. In particular, U-shaped clip 81 includes a pair of legs or wall 82, 84 with a yoke 86 extending therebetween. Also, formed in each leg 82, 84 is an aperture 87, 88, respectively, which is intended to pass shaft 14 freely therethrough in a first or loaded position of the clip 81 such as with legs 82, 84 being generally vertically oriented or parallel to each other as seen in FIG. 12, and to otherwise grip the surface of shaft 14 when the clip 81 is in a second or unloaded state as shown in FIG. 13, such as with legs 82, 84 being angularly (advantageously outwardly in the direction of arrows 89 and 89' in FIG. 13) offset from the positions they had in FIG. 12.

Clip 81 is advantageously a piece of resilient spring metal or shaped plastic such that it normally tends into the second state (FIG. 13), but can be bent or flexed into the first state seen in FIG. 12. The dual leg aspect of clip 81 provides an advantageous bi-directional grip on needle shaft 14 such that clip 81 may be sufficient to define a needle tip protector. To this end, clip 81 may be contained within housing 64, which may also be the housing to support the apertured members 28, 30 or 28', 30' (not shown in FIGS. 12 and 13), if desired. The proximal and distal walls 66, 68 of housing 64 each allow shaft 14 to pass therethrough, but not clip 80.

A trigger mechanism 90 may be provided for clip 81. In particular, trigger mechanism 90 has a base wall 92 with a front retainer 94 defining an aperture or slot 96 therein sized to receive needle shaft 14 therethrough in the needle loaded position of FIG. 12. With needle shaft 14 extending through aperture 96, base wall 92 is held in fixed spaced relation to shaft 14 such that clip legs 82, 84 may be held in the first state between upstanding clip ledges 100, 102 of base wall 92. Ledges 100, 102 may be defined by the end surfaces of cutout or depression 104 of base wall 92. When needle 12 is moved in the direction of arrow 37 (FIG. 12) to the unloaded position, such as shown in FIG. 13 by way of example, mechanism 90 tilts or falls away (as indicated by arrow 106 in FIG. 13) from needle shaft 14, thereby releasing legs 82, 84 so that they may take on the second position to grip shaft 14. To facilitate a tilting action, trigger mechanism 90 may be a resilient metal or plastic strip pivotally hinged to proximal wall 66 of housing 64 and biased thereby downwardly, and/or may include one or more springs (not shown) to provide the bias.

In the unloaded state, seen in FIG. 13, the needle tip 16 is held inside housing 64. Housing 64 may be provided with one or more cams 110, 112 positioned outwardly of legs 82, 84. Each cam 110, 112 cooperates to urge respective legs 82, 84 of clip 81 into being further angularly offset in response to pushing or pulling of needle 12. In particular, if needle 12 is pulled to the right in FIG. 13, clip leg 84 will bear against surface 114 of cam 112 causing leg 84 to attempt to pivot further outwardly in the direction of arrow 89' to thus further enhance the grip of leg 84 on needle shaft 14 by leg 84. Similarly, if needle 12 is pushed to the left in FIG. 13, clip leg 82 will bear against surface 116 of cam 112 causing leg 82 to attempt to pivot further outwardly in the direction of arrow 89 to thus further enhance the grip of leg 82 on needle shaft 14. To enhance the pivot tendency of legs 82, 84, surfaces 114 and 116 may extend at an angle from a plane 118 perpendicular to the needle shaft 14, with the angle matching the normal angular offset of the associated clip leg 82 or 84 in the second state, by way of example.

Although clip 81 is shown within a relatively rigid housing 64 which also advantageously houses trigger mechanism 90, it will be appreciated that some portion or all of the containment and/or trigger mechanism for clip 81 could be provided by protector 10, by way of example.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. By way of example, in the case of use with a catheter 52, tip protectors 10 and 10' may be held to catheter hub 56 by directly (or indirectly via fingers 70, 72) interacting with the interior wall 54 of hub 56. Alternatively, tip protector 10 or 10' could be held to catheter hub 56 (directly or indirectly) by interaction with the exterior of catheter hub 56. Additionally, support member 20 and its related aperture 22 may serve to align tip protector 10 or 10' and/or housing 64, depending upon the overall thickness and aperture size defined by support member 20. Further, a Teflon felt wiper (not shown) may be placed within housing 64 to help contain blood (also not shown) which might find its way onto the needle shaft 14. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A safety catheter comprising:
   a catheter assembly including a catheter hub with an interior cavity, and a catheter tube extending distally from the catheter hub and in fluid communication with the catheter hub cavity;
   a needle having a sharp tip at a distal end of a needle shaft;
   a housing having a proximal end with an opening for the needle and a sidewall extending distally of the proximal end, the housing having a cavity bounded at least in part by the sidewall and through which the needle shaft can pass along a needle path and a pair of resilient arms carried with the housing, the arms extending along the cavity alongside the sidewall and distally along the needle path, each of the arms supporting a member aimed at the needle path, the housing, arms and members being sized so as to extend into the catheter hub cavity, the arms being moveable relative to the sidewall between a first position wherein the members do not block the needle path and a second position wherein the members block the needle path;
   a first state being defined by the housing and arms extending into the catheter hub cavity and the members situated within the catheter hub cavity, the needle shaft extending through the housing cavity and catheter assembly with the tip exposed distally of the catheter tube, and the arms being held in the first position;
   a second state being defined by the needle tip in the housing cavity proximal of the members and the arms being in the second position.

2. The safety catheter of claim 1 wherein the arms are held to the housing.

3. The safety catheter of claim 1, the housing including a proximal wall with an aperture for the needle shaft to pass therethrough, the arms extending distally from opposite sides of the aperture.

4. The safety catheter of claim 3, the arms being held to the proximal wall.

5. The safety catheter of claim 1, the members being supported at respective distal ends of the arms.

6. The safety catheter of claim 1, the members slidably engaging the needle shaft in the first state.

7. The safety catheter of claim 1, the arms being biased toward the second position.

8. The safety catheter of claim 7, the members slidably engaging the needle shaft in the first state such that the arms are held in the first position by the needle shaft.

9. The safety catheter of claim 1, the catheter hub having a sidewall defining the interior cavity, the arms and members being spaced from the catheter hub sidewall in the second position.

10. The safety catheter of claim 9, the arms supporting edges situated to engage the catheter hub sidewall in the first position.

11. The safety catheter of claim 10, the edges being defined on the members.

12. The safety catheter of claim 11, the edges being defined by the members.

13. The safety catheter of claim 1, the needle shaft including an irregularity thereon near the distal end of the needle shaft.

14. The safety catheter of claim 1, the housing being plastic and the arms being metal.

15. The safety catheter of claim 1 further comprising a needle hub from which the needle shaft extends, the needle hub being movable relative the housing between the first state and the second state.

16. The safety catheter of claim 1, the housing being generally cylindrical.

17. The safety catheter of claim 1, the housing sidewall being continuous to define the housing cavity therewithin.

18. The safety catheter of claim 17, the arms being confined within the housing cavity.

19. The safety catheter of claim 1, the arms being confined within the housing cavity.

* * * * *